United States Patent [19]

Hamer

[11] 4,151,832
[45] May 1, 1979

[54] SERUM ABSTRACTION DEVICE

[76] Inventor: Geerd Hamer, 6101 Weiterstadt, Vorm Heiligen Kreuz 15, Fed. Rep. of Germany

[21] Appl. No.: 779,495

[22] Filed: Mar. 21, 1977

[30] Foreign Application Priority Data

Mar. 19, 1976 [DE] Fed. Rep. of Germany ....... 2611721

[51] Int. Cl.² ............... A61M 1/00; A61B 17/28; G01N 33/16
[52] U.S. Cl. ............... 128/765; 128/278; 210/DIG.23; 422/56; 422/58; 422/68; 128/771
[58] Field of Search ............... 128/2 F, 278, DIG. 5; 23/259, 292; 210/DIG. 23; 422/56, 58, 68

[56] References Cited

U.S. PATENT DOCUMENTS

| | | | |
|---|---|---|---|
| 3,448,041 | 6/1969 | Swank | 210/DIG. 23 |
| 3,610,242 | 10/1971 | Sheridan | 128/2 F X |
| 4,036,232 | 7/1977 | Genese | 128/2 F X |

*Primary Examiner*—Sidney Marantz

[57] ABSTRACT

A vacuum housing connected to a vacuum generator has one open end covered by a fine sieve to provide a serum collection space. A test strip of blotting paper is flush against an intermediate air permeable membrane which is in turn flush against a support sieve.

7 Claims, 2 Drawing Figures

SERUM ABSTRACTION DEVICE

BRIEF SUMMARY OF THE INVENTIONS AND ITS OBJECTS

The present invention relates to a device for extracting tissue serum.

It is already known in the art how to extract blood through a hypodermic needle. This always requires a skin puncture, a skilled hand, is unpleasant for the patient and requires high-precision hand tools. The procedure must be very aseptic. In addition, a puncture leaves a scar. It is the purpose of the present invention to provide a device which requires much lesser amounts of serum, and possibly permits an immediate diagnosis and with which serum can be extracted at various locations of the body without puncture.

This object of the present invention is achieved through the following characteristics:

a. There is an underpressure housing whose one open end is covered by a fine sieve.

b. A serum collecting space is provided in the underpressure housing within the sieve.

c. The underpressure housing is connected to an underpressure generator.

Advantageously a test strip is introduceable in an essentially airtight manner into the serum collecting space. Through these improvements it is possible to quantitatively determine the desired laboratory value on a specially prepared blotting paper as a quick reaction immediately after extracting the tissue serum.

Advantageously, the test strip is located directly behind the sieve. Through these improvements, the required serum quantity becomes a minimum. The serum might also be taken by a cuvette from the serum collecting space.

Advantageously, a support sieve for the test strip is in flush contact with one side of the test strip. Through these improvements, the test strip lies flush and is not removed by suction.

Advantageously, the underpressure housing has the form of a tube. Through these improvements, one obtains a simple manufacturing process, combined with prehensility and the possibility to introduce the device into body cavities. For example, the device can be easily placed against the oral cavity mucous membrane, the clitoral glans, the mucuous membrane of the gastrointestinal tract, etc.

The device can be used aseptically in a simple manner, by placing it after every use into a special cleaning fluid in order to eliminate any transmission of disease.

DESCRIPTION OF THE DRAWING

The drawing shows a preferred embodiment.

DETAILED DESCRIPTION

Figure 1:
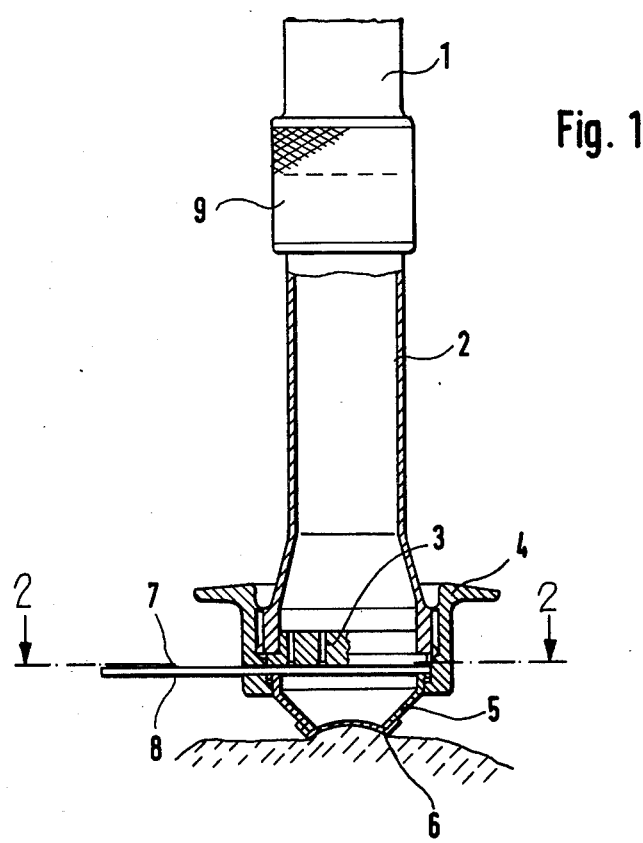
FIG. 1 shows a sideview of the device, partially cut radially.

On top is a vacuum pump connection 1 which can be connected to a vacuum cylinder 2. The lower end of the vacuum cylinder 2 has a support sieve 3 which has several axial boreholes. A clamping ring 4 with hand rest clamps a suction stub 5 from below against the support sieve 3. The suction stub 5 is open below, but covered with a suction sieve 6 which is a narrow-mesh wire grid. From the left, a porous packing intermediate wall 7 is inserted which is flush with the support sieve 3 and against which blotting paper 8 is placed at the bottom. The packing intermediate wall 7 permits the passage of air, but not of serum. The blotting paper 8 is of the type used in laboratory diagnosis, e.g., for quick reactions, for quantitative determinations. The suction sieve 6 prevents the skin from being sucked in more than required. Sleeve 9 has an internal screw thread for connecting the connection 1 to the vacuum cylinder 2. The components cooperate to collect a serum sample in the following manner.

The suction stub 5 is inserted from above down into the clamping ring 4. Because the upper outer diameter of the suction stub 5 is larger than the lower inner diameter of clamping ring 4, the suction 3 is inserted from above into the clamping ring 4 and lies above of suction stub 5. The support sieve 3 has an outer flange the diameter of which equals to the outer diameter of vacuum cylinder 2.

The clamping ring 4 has an inner thread and the vacuum cylinder 2 in its lower area has an outer thread. Now clamping ring 4 with its inserts 5 and 3 is threaded from below upward against the vacuum cylinder 2.

Figure 2:
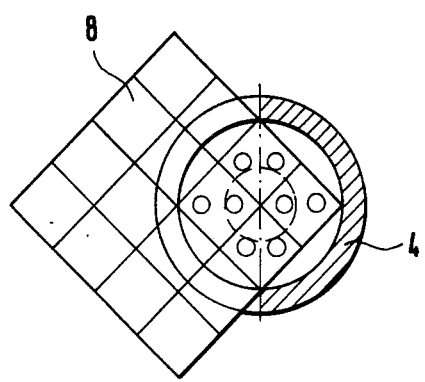
FIG. 2 shows a section taken along line 2—2 in FIG. 1.

For inserting the blotting paper 8 the insert ring 4 has a slot from the left as seen in FIGS. 1 and 2 and through this slot the blotting paper 8 may be inserted. The slot in the clamping ring 4 is such, that the wall 7 is flush with the lower face of support sleve 3.

Blotting paper 8 has several areas which may be chemically prepared in several ways, e.g., the 4 corners may be prepared with four different agents.

FIG. 2 shows that, with proper placing of the boreholes in support sieve 3, square blotting paper divided into four large squares each divided into four small squares may be used. Then a large square may be used for one analysis and the four small squares for the individual diagnosis.

The underpressure is made adjustable because the human skin has different thickness at different locations. When using on mucous membrane, the underpressure must be small, while the underpressure with use against scarf-skin may be somewhat greater.

The device may also be coupled with gastro capsules if, e.g., tissue serum is to be obtained from the gastrointestinal tract. The devicce can also locate local expansions, e.g., in cancer research, or the tissue oxygen activity can be determined.

In operation, the suction sieve 6 is placed against the portion of the skin from which the serum sample is to be taken. The underpressure partial vacuum action within the connection 1 and the vacuum cylinder 2 draws the serum without puncturing the skin, as would be the case with a syringe or needle. A very short distance behind the sieve 6, a corner of the blotting paper 8, backed by the air pourous wall 7, is supported by the fixed support sieve 3 against being sucked upward into the vacuum cylinder 2. The blotting paper is of the type used for quick reactions in laboratory diagnosis. Since the blotting paper 8 is close to the sieve 6 and the wall 7 prevents serum (but not air) from passing into the vacuum cylinder 2, extremely small quantities of body fluid are required, immediate reaction is observed on the blotting paper 8, and the suction time is quite short.

I claim:

1. A device for the extraction of tissue serum comprising a vacuum housing having an open end, a fine sieve covering said open end and positioned to directly contact said tissue in use to define a serum collecting space in said vacuum housing behind said sieve, a test strip in said serum collecting space a short distance from said fine sieve.

a support sieve for said test strip on one side of said test strip, and means for connecting said vacuum housing to a vacuum generator, whereby said serum is drawn through said sieve into said collecting space.

2. The device as defined in claim 1 wherein said test strip is introduceable in an essentially airtight manner into said serum collecting space.

3. The device as defined in claim 1 wherein said vacuum housing has the form of a tube.

4. The device as defined in claim 1 wherein said test strip is located directly behind said sieve.

5. The device as defined in claim 1 wherein said support sieve for said test strip is in flush contact with one side of said test strip.

6. The device as defined in claim 1 wherein said sieve is concave.

7. The device as defined in claim 1 comprising a membrane permeable only to air located between said test strip and said support sieve.

* * * * *